(12) United States Patent
Becker et al.

(10) Patent No.: US 7,628,613 B2
(45) Date of Patent: Dec. 8, 2009

(54) DEVICE FOR COUPLING DENTAL INSTRUMENTS

(75) Inventors: Arie Becker, Kibbutz Afikim (IL); Gabriel Savin, Rishon LeZion (IL); Nachman Berger, Ramat Gan (IL); Yalon Fishbein, Kibbutz Afikim (IL)

(73) Assignee: Medic.NRG Ltd., Kibbutz Afikim (IL)

( * ) Notice: Subject to any disclaimer, the term of this patent is extended or adjusted under 35 U.S.C. 154(b) by 0 days.

(21) Appl. No.: 11/487,626

(22) Filed: Jul. 17, 2006

(65) Prior Publication Data

US 2007/0026362 A1    Feb. 1, 2007

(30) Foreign Application Priority Data

Jul. 28, 2005  (IL) .................................... 169951

(51) Int. Cl.
*A61C 1/08* (2006.01)
(52) U.S. Cl. ...................................... 433/126
(58) Field of Classification Search ............... 433/27, 433/32, 72, 102–131; 600/587–590
See application file for complete search history.

(56) References Cited

U.S. PATENT DOCUMENTS 5,897,315 A * 4/1999 Nakayama et al. ............ 433/72
5,902,105 A * 5/1999 Uejima et al. ................ 433/27
6,520,773 B1 * 2/2003 Weber .......................... 433/27
7,070,411 B2 * 7/2006 Nakanishi et al. ............. 433/72

FOREIGN PATENT DOCUMENTS

| DE | 195 49 662 C2 | 11/2002 |
| EP | 1 563 803 A | 8/2005 |
| JP | 09 056734 A | 3/1997 |
| JP | 2000 254149 A | 9/2000 |
| JP | 2001 309932 A | 11/2001 |
| JP | 2004 000554 A | 1/2004 |

* cited by examiner

*Primary Examiner*—Ralph A Lewis
*Assistant Examiner*—Sunil K Singh
(74) *Attorney, Agent, or Firm*—Karl F. Milde, Jr.; Eckert Seamans Cherin & Mellott, LLC

(57) ABSTRACT

There is provided a coupling device for electrically coupling a dental instrument to an electrical connector, including a tubular clasp made of an electrically conductive material having a first portion attachable to the connector and a second portion attachable to the dental instrument, the second portion having a slot facilitating insertion and holding of the dental instrument while performing a dental procedure.

5 Claims, 5 Drawing Sheets

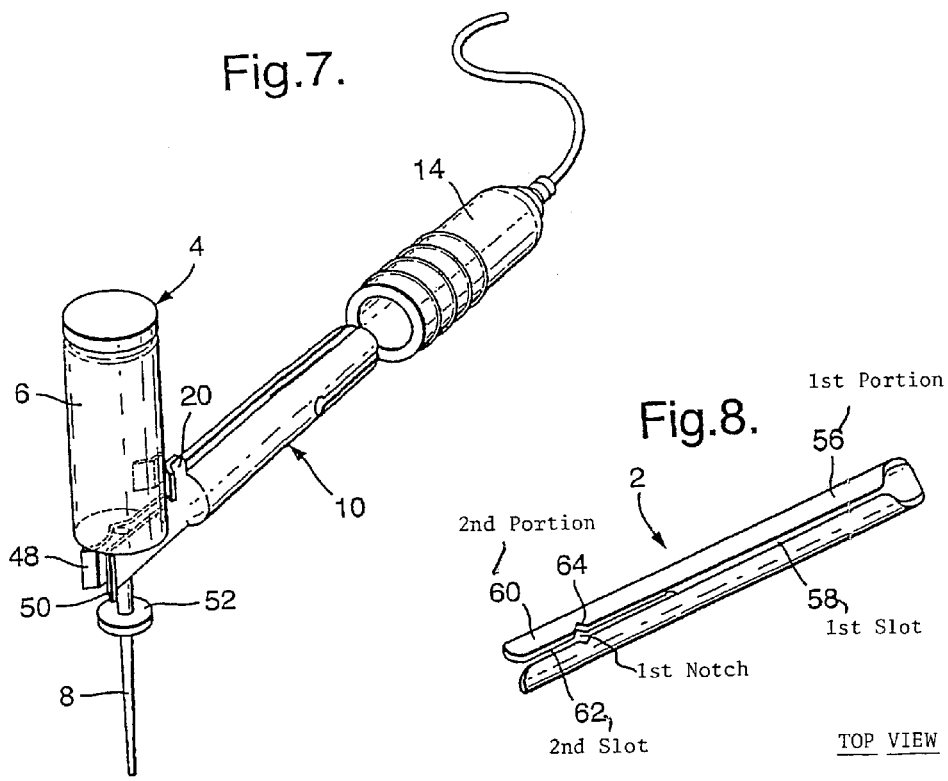
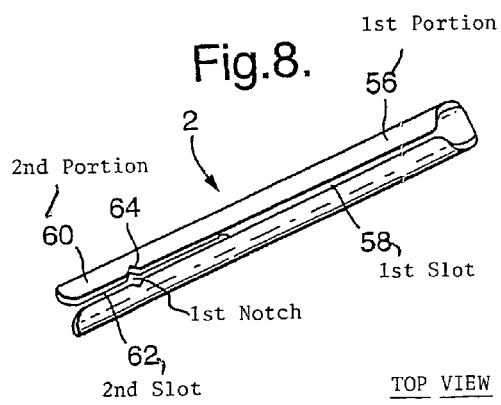
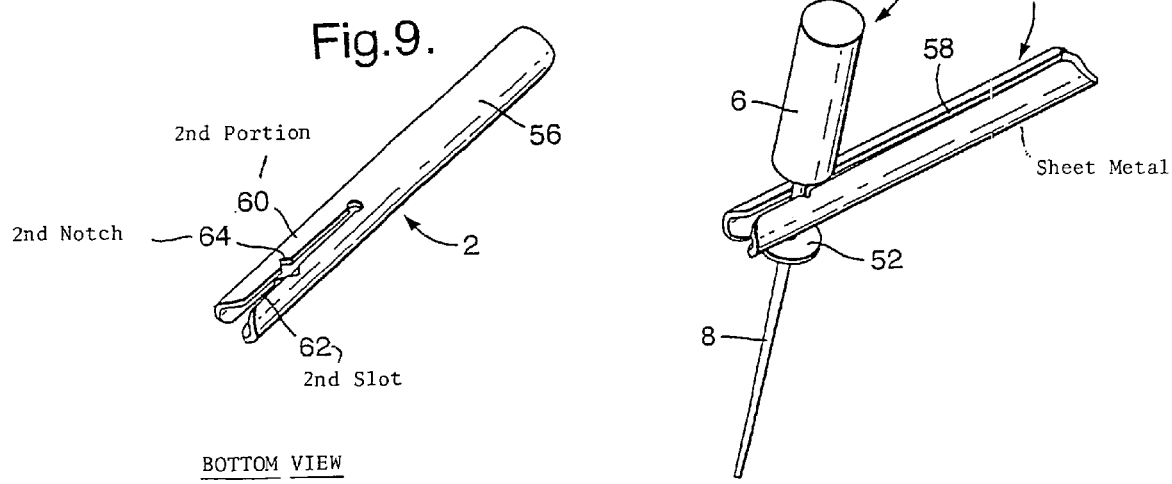

DEVICE FOR COUPLING DENTAL INSTRUMENTS

FIELD OF THE INVENTION

The present invention relates to a dental system and more particularly to a coupling device for coupling a dental instrument for use in dental work.

BACKGROUND OF THE INVENTION

There are known many types of portable holders for supporting and handling exchangeable delicate instruments for dental work, all of which are somewhat cumbersome, thus making it difficult to perform delicate dental work.

Moreover, with the constant increase of contagious plagues and diseases, such as Aids, SARS and the like, special attention and care should be given to proper sterilization of such instruments, as well as holders. The cost involved in sterilization is high, especially for sterilizing relatively larger components such as instrument holders.

DISCLOSURE OF THE INVENTION

It is therefore a broad object of the present invention to overcome the disadvantages of the known types of dental instrument holders and/or couplers.

It is a further object of the present invention to provide a dental instrument coupling device, which is relatively smaller than the prior art holders, lightweight and comfortable for use in performing delicate work.

It is still a further object of the present invention to provide a dental instrument coupling device which is not expensive, thus rendering it disposable after use, saving the further cost of the requirement for sterilization.

Still a further object of the invention is to provide a coupling device for dental instruments which is electrically conductive.

In accordance with the present invention, there is therefore provided a coupling device for electrically coupling a dental instrument to an electrical connector, said device comprising a tubular clasp made of an electrically conductive material having a first portion attachable to said connector and a second portion attachable to said dental instrument, said second portion having a slot facilitating insertion and holding of said dental instrument while performing a dental procedure.

BRIEF DESCRIPTION OF THE DRAWINGS

The invention is herein described, by way of example only, with reference to the accompanying drawings.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 is an isometric view of a first embodiment of the coupling device and a dental instrument in use, according to the present invention;

FIG. 2 is an isometric view of the coupling device of FIG. 1 alone;

FIG. 3 is a blank for producing the coupling device of FIG. 2;

FIG. 4 is an isometric view of a second embodiment of a coupling device, according to the present invention;

FIG. 5 is an isometric view of the coupling device of FIG. 4, supporting a dental instrument;

FIG. 6 is an isometric view of a further embodiment of the coupling device, according to the present invention;

FIG. 7 is the coupling device of FIG. 6, electrically connecting a dental instrument to an electrical socket;

FIGS. 8 and 9 are isometric views showing opposite sides of another embodiment of the coupling device according to the present invention.

FIG. 10 is an isometric view of the coupling device of FIGS. 8 and 9, holding a dental instrument;

FIG. 11 is an exploded view, to a reduced scale, of a dental system employing the coupling device according to the present invention, with an actuator, and FIG. 12 illustrates the dental system of FIG. 11 in an assembled state.

DETAILED DESCRIPTION

Figure 1:
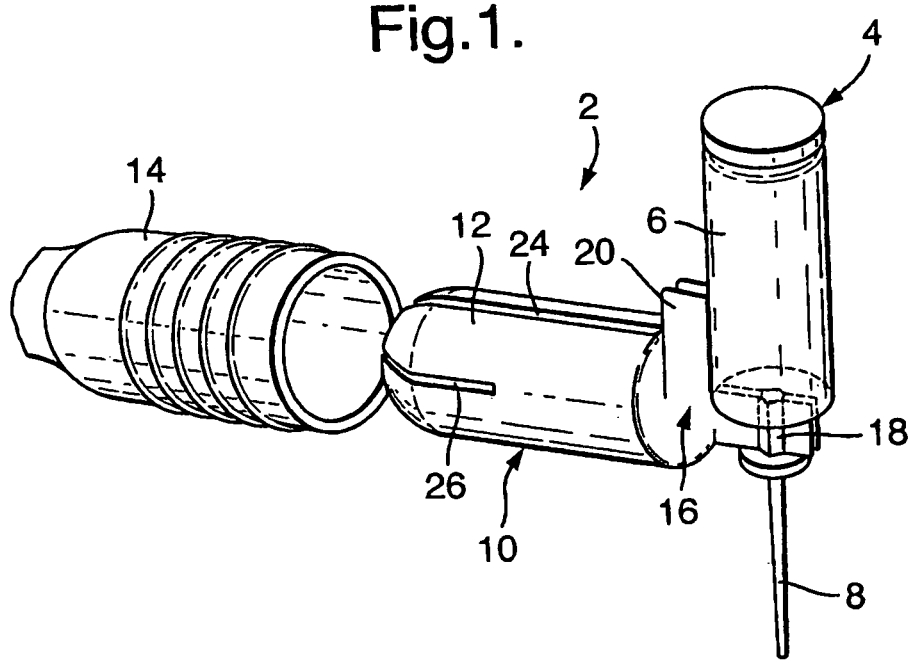
Figure 2:
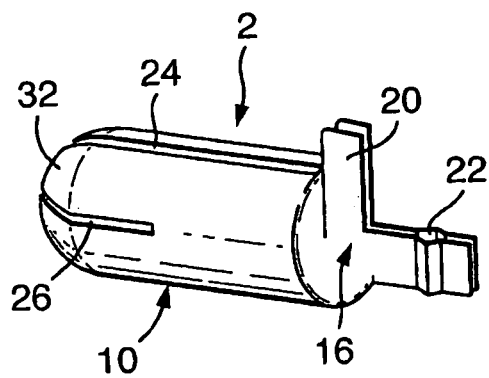

Referring now to the drawings, there is illustrated in FIGS. 1 and 2 a coupling device 2 for a dental instrument 4, e.g., in the shown figure a dental file composed of a handle 6 and a filing shaft 8. The coupling device 2 has a first tubular portion 10 having a first end 12 attachable to a connector 14, in the shown embodiment, configured as a socket tube. The second portion 16 forms a seat 18 and an abutting shoulder 20, to the dental instrument 4. The seat 18 is formed by a through-going passage 22 formed in between two resiliently contacting members of the second portion, as will be described in greater detail with respect to FIG. 3. Also seen in FIGS. 1 and 2 are a slot 24 extending along the entire length of the coupling device 2 and a short cut or slot 26.

Figure 3:
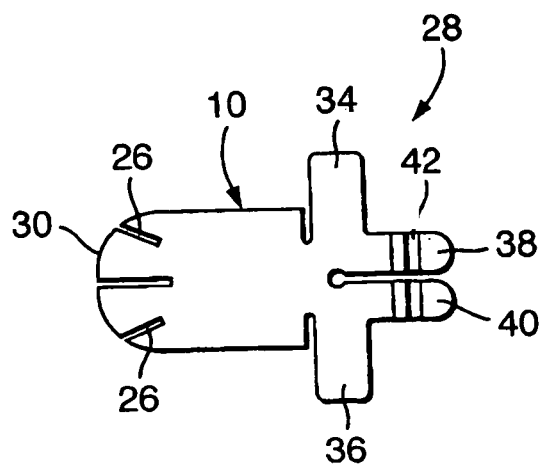

Turning now also to FIG. 3, there is depicted a blank 28 from which, advantageously, the coupling device 2 can be made. The blank 28 is stamped out from a sheet of resilient material preferably, an electrically conductive material. The first and second portions 10 and 16 are integrally made. The first portion 10 is generally rectangular, having a rounded end 30, in which a plurality of spaced-apart short cuts/slots 26 are made to facilitate the forming of a spherical edge 32 (FIG. 2). The two oppositely extending tabs 34, 36 form the shoulder 20 when the blank 28 is rolled up into the tubular portion 10. At least one of the finger-like members 38, 40 forming the seat 18 is made with an indent 42, so that upon the rolling up of the first portion 10 and the folding of the second portion 16, there is formed the through-going passage 22. The size of the tabs 34, 36 and of the members 38, 40 is predetermined by the size of the dental instrument(s), which it is intended to support. The slot 24 renders the tubular first portion 10 to be springy, facilitating positive connection with the connector 14. Similarly, the configuration of the members 38, 40, results in a springy clamping action around the dental instrument 4.

Figure 4:
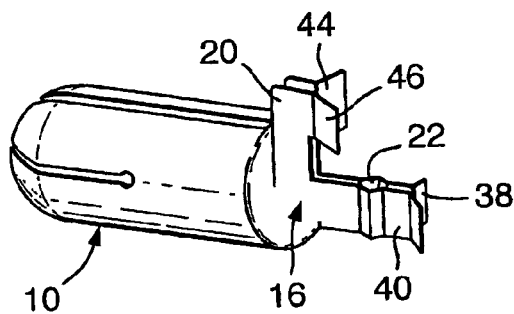
Figure 5:
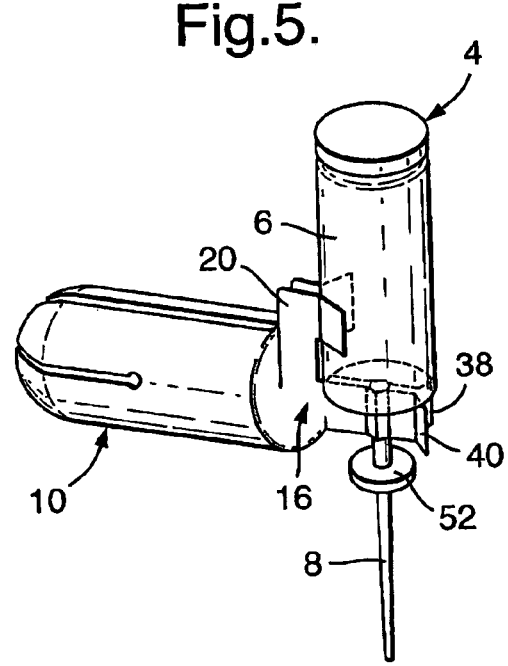

FIGS. 4 and 5 show a modification of the embodiment of FIGS. 1 to 3 in which the tabs 34, 36 are formed with outwardly flaring wings 44, 46 for better gripping of the handle 6 of the dental instrument 4.

Figure 6:
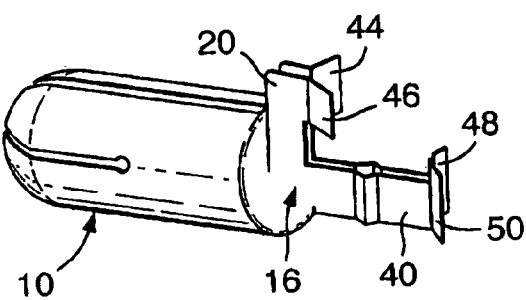

Referring to FIGS. 6 and 7, a still further embodiment is shown according to which the members 38, 40 are made with extensions 48, 50 projecting in the same direction as the shoulder 20, so as to provide an abutment to the lower side of the handle 6 of the dental instrument 4.

As more clearly illustrated in FIGS. 4 to 7, the dental instrument 4 may be furnished with a disc 52, slidingly engageable to the stem of the filing portion 8, after insertion in the passage 22, for supporting the instrument in place also from underneath the seat 18.

Figure 11:
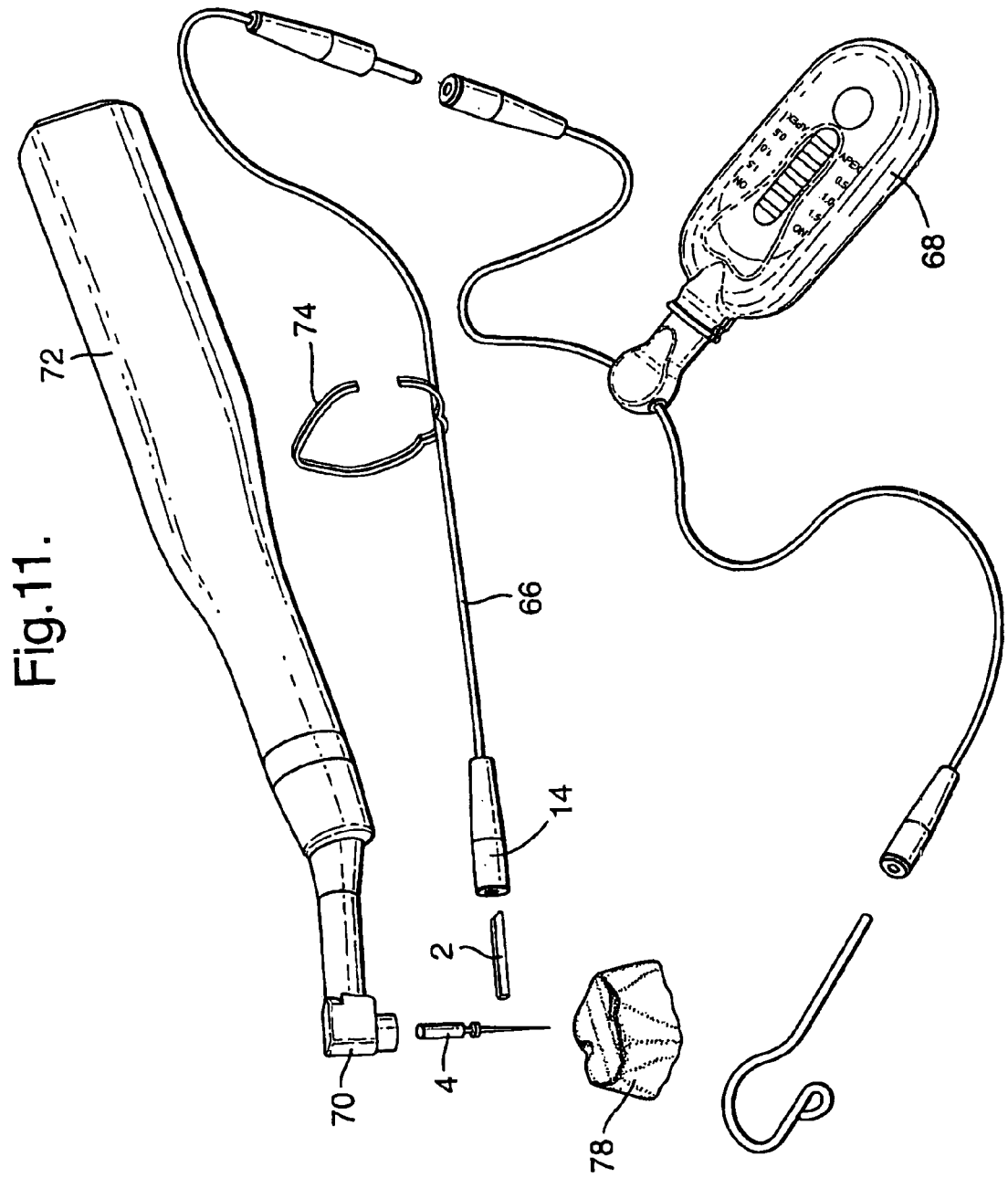
Figure 12:
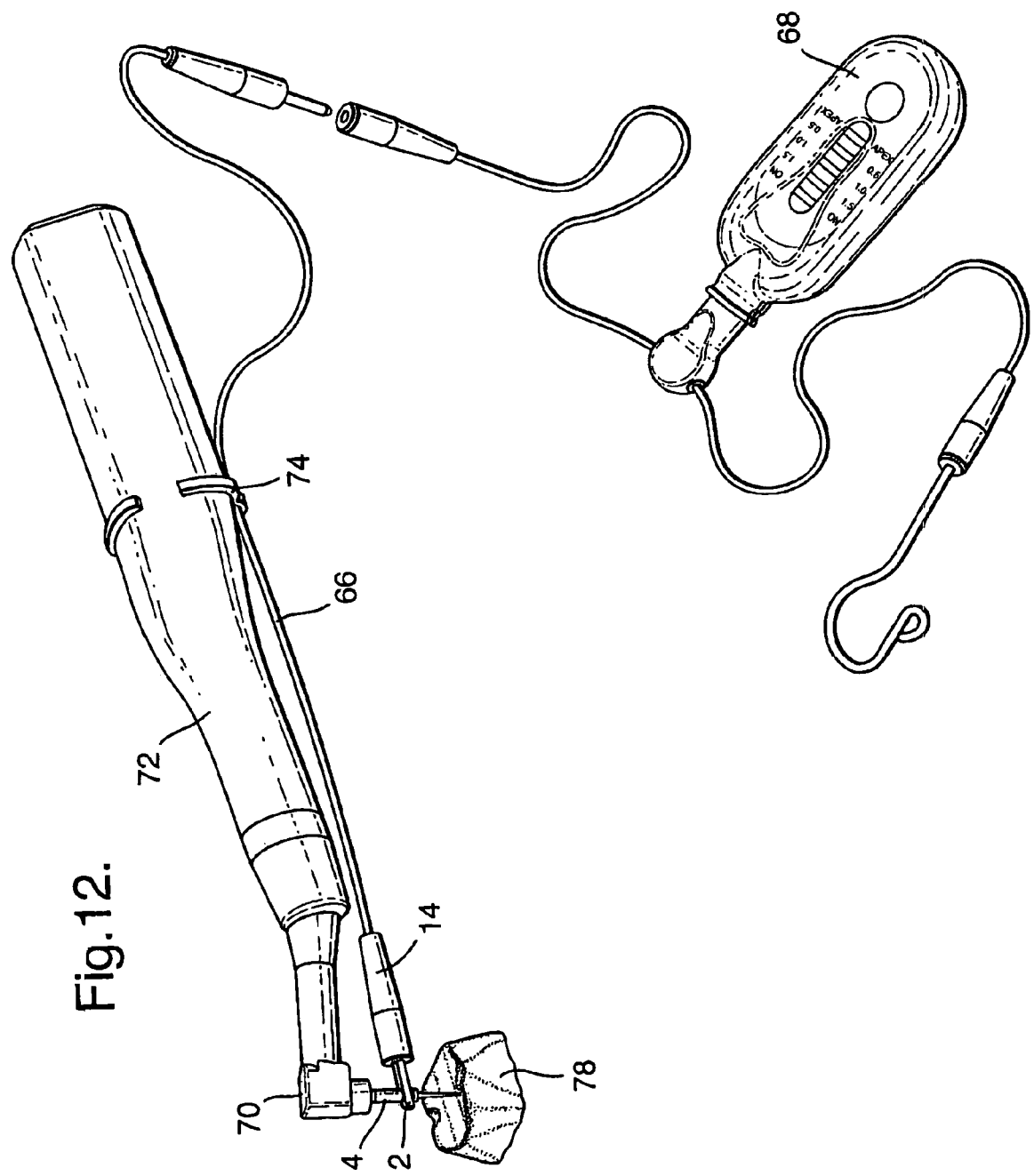

As described hereinbefore, the coupling device 2 is advantageously made of electrically conductive material so that low electrical current can pass from the filing shaft 8 of the dental instrument to the connector 14, which in turn, is wired to e.g., an apex locator, shown in FIGS. 11 and 12, which measures and provides a continuous indication of the canal depth formed by the drilling or filing instrument during treatment.

Referring to FIGS. 8 to 10, there is illustrated a further embodiment of a dental instrument coupling device 2 having a configuration of a tubular clasp. The coupling device 2 is made of an electrically conductive material, having a first portion 56 made on one side with a first slot 58 and a second portion 60 also including a second slot 62 opposite the first slot 58 and aligned therewith. The purpose of the first slot 58 in the first portion 56 is to render the first portion resilient, so as to facilitate easy and positive connection to an electrical connector 14, e.g., a socket. The purpose of the second slot 62 is to form two resiliently extending members, facilitating the insertion of a dental instrument 4. Such an instrument may be constituted by a dental file having a handle 6, a filing shaft 8 and a disc 52. A notch 64 for grasping instruments 4 of different sizes is advantageously provided on opposite sides of the second slot 62.

Turning now to FIG. 11, there is illustrated the coupling device 2 connectable to a connector 14, leading via cable 66 to a per-se known apex locator 68. Also seen is the dental instrument 4 suitably oriented to be attached to a head portion 70 of an actuator 72 e.g., a dental handpiece. For convenience during use, the cable 66 is affixable along the actuator 72 by means of a holder ring 74. The assembled system, including the dental instrument 4 is attached to the actuator 72 for communicating motion to it, the electrical coupling device 2 as connected to the connector 14, is shown in FIG. 12 in an operative state, as disposed above a tooth 78, to be treated.

As can be realized the coupling device 2 facilitates utilizing different kinds of actuators, e.g., handpieces, performing dental tasks requiring monitoring by an apex locator. Furthermore, the coupling device of the present invention is easily detachable from, and connected to, the dental system for replacement or for the purpose of thorough cleaning and disinfecting, without having to clean and disinfect the entire actuator.

It will be evident to those skilled in the art that the invention is not limited to the details of the foregoing illustrated embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A coupling device for mechanically and electrically coupling a dental instrument to an electrical connector, said device comprising:
    a tubular clasp made of an electrically conductive resilient material having a first cylindrical portion attachable to said connector and a second cylindrical portion attachable to said dental instrument;
    said first cylindrical portion having a first slot that extends axially along an outer cylindrical surface of the tubular clasp;
    said second cylindrical portion having a second slot that extends axially along an outer cylindrical surface of the tubular clasp opposite the first slot and in alignment therewith; and
    said second cylindrical portion having a first notch formed in the second slot in the cylindrical outer surface of the tubular clasp on one side of the clasp and having a second notch formed in the second slot in the cylindrical outer surface of the tubular clasp on an opposite side of the clasp so that the first notch and the second notch are aligned, whereby insertion of a dental instrument into the first notch and the second notch in the second slot causes opposite sides of the second portion of the tubular clasp to resiliently splay apart to accommodate said dental instrument and to hold said dental instrument while performing a dental procedure.

2. The coupling device as claimed in claim 1, wherein the first slot extends along substantially a complete length of the tubular clasp.

3. The coupling device as claimed in claim 1, wherein said electrical connector includes a socket that is electrically connectable to an apex locator.

4. The coupling device as claimed in claim 1, wherein said dental instrument is a dental file.

5. The coupling device as claimed in claim 1, wherein said dental instrument is configured to be coupled to an actuator for communicating motion to it.

* * * * *